United States Patent [19]

Mittleman

[11] Patent Number: 4,538,918
[45] Date of Patent: Sep. 3, 1985

[54] MEDICATION MIXING AND SEQUENTIAL ADMINISTRATION DEVICE

[75] Inventor: Herbert Mittleman, Deerfield, Ill.

[73] Assignee: Trimedyne, Inc., Santa Ana, Calif.

[21] Appl. No.: 533,124

[22] Filed: Sep. 19, 1983

[51] Int. Cl.³ .............................................. B01F 15/04
[52] U.S. Cl. .................................... 366/160; 366/161; 366/173; 366/182; 222/133; 604/81
[58] Field of Search ..................... 137/99; 222/57, 133, 222/135, 145; 366/131, 150, 152, 160, 161, 162, 167, 173, 177, 179, 182; 604/80, 81, 82, 83, 85, 56, 251

[56] References Cited

U.S. PATENT DOCUMENTS

| | | | |
|---|---|---|---|
| 2,440,365 | 4/1948 | Copping | 222/133 |
| 2,529,028 | 11/1950 | Landon | 222/57 |
| 4,120,424 | 10/1978 | Zygiel | 222/133 |
| 4,166,084 | 8/1979 | Shea | 222/133 |
| 4,324,238 | 4/1982 | Genese | 604/81 |
| 4,417,577 | 11/1983 | Genese | 604/81 |

FOREIGN PATENT DOCUMENTS 854926  11/1970  Canada ................................. 222/133

Primary Examiner—Robert W. Jenkins
Assistant Examiner—Arthur D. Dahlberg

[57] ABSTRACT

The present invention teaches a medical device which mixes a primary medication with a secondary medication before administration to a patient. The device is also capable of automatically sequentially administering the primary medication alone to the patient. The device includes a medication chamber which is reduced in volume to deliver the secondary medication for mixing with the primary medication.

16 Claims, 2 Drawing Figures

MEDICATION MIXING AND SEQUENTIAL ADMINISTRATION DEVICE

TECHNICAL FIELD OF THE INVENTION

The present invention relates to medical devices for the mixing and delivery of medication by infusion.

BACKGROUND OF THE INVENTION

It is common to administer a diluted secondary medication intravenously to a patient followed by a primary medication. A commonly used system is referred to as a piggy-back setup. Generally, a catheter is located in a patient's vein and connected by a delivery tube to a "Y" connector. One branch of the connector is coupled through a one-way valve to a primary reservoir which contains the primary medication such as saline. The other branch of the connector is coupled with a secondary reservoir into which the secondary medication is placed. The secondary medication can be a drug diluted in a liquid vehicle such as saline.

For proper operation, the secondary reservoir is hung at a higher elevation than the primary reservoir. The secondary medication then has a greater pressure head than the primary medication. This pressure difference keeps the valve closed so that only diluted secondary medication flows to the patient. When the secondary reservoir is exhausted, its pressure head decreases to zero and the valve opens. The primary medication then flows to the patient. For examples of piggy-back setups, see U.S. Pat. Nos. 3,886,937 to Bobo et al. and 4,372,306 to Genese et al.

Unfortunately, such systems require two reservoirs, one for the primary medication and one for the secondary medication. The amount of secondary medication dilution is restricted by the size of the secondary reservoir. The liquid level in the secondary reservoir must also be maintained at a greater height than the liquid level in the primary reservoir. Such systems further require two separate sets of tubing, a connector, a valve, and related flow regulation apparatus. Such an extensive amount of equipment not only complicates the use of the system, but also adds to its cost.

It is also possible for the valve to stick open causing a mixture of the secondary medication with the primary medication. This changes the rate and dilution of medication from that which has been prescribed. The flow regulation apparatus in such systems is usually associated with the delivery tube below the "Y" connector. This causes difficulties in selecting and maintaining the administration rate as the relative reservoir pressure heads vary.

To avoid some of these problems and provide for a greater range of medication dilution, a second type of system has been developed. This system uses a burette connected by a first tube to a primary reservoir. The desired secondary medication is injected into the burette and the appropriate amount of primary medication is added from the primary reservoir. The air displaced by the primary medication is vented out of the burette through a filter material. The flow through the first tube is stopped and the diluted medication is administered through a second tube to the patient as air enters the burette through the filter material. If desired, more medication can be diluted or the flow of primary medication through the first tube restarted to flow on to the patient.

While this system avoids some of the problems of the previously discussed system, it has its own shortcomings. Among these are the possibility of contamination entering through the filter material as the medication solution is delivered. It is not possible to automatically sequentially deliver the primary medication after the delivery of the secondary medication has been completed. An operator must return to adjust the flow regulator after the delivery of the secondary medication has been completed.

Accordingly, it would be desirable to avoid the difficulties encountered with present systems and provide a device which provides for uniform and adjustable dilutions of medication. The device should also be able to automatically administer the primary medication alone after the desired amount of secondary medication has been administered. It would be further desirable if such a device were easy to set up, inexpensive to manufacture, and relatively simple to use. The present invention meets these desires.

SUMMARY OF THE INVENTION

The present invention is a medication mixing and delivery device which defines a continuous flow path for a primary medication and allows for the controlled mixing of a secondary medication into the primary medication and their combined administration to a patient. After the secondary medication has been delivered, the device sequentially continues to administer the primary medication without the need for a further adjustment.

The primary and secondary medications are contained in separate reservoirs and can be infused into the patient at independently regulated rates. The primary medication, such as saline, dextrose, or the like, which can be a diluent for the secondary medication is provided from an elevated source such as a collapsible bag commonly used in intravenous administration. The secondary medication is received in a first variable volume space or chamber defined in part by a housing forming part of the device of the present invention. The device also includes a mixing cell mounted on the housing. The primary and secondary medications follow separate flow paths to enter the mixing cell where they are mixed prior to administration to the patient.

The primary medication enters the device through an inlet on the housing and flows through the device in a continuous primary flow path to the mixing cell. The primary flow path is also in fluid communication with a volume reducing means for reducing the volume of the variable volume chamber. This delivers the secondary medication from the chamber to the mixing cell via a secondary medication fluid passageway so as to mix with the primary medication in the mixing cell.

The volume reducing means preferably includes a second variable volume space or enclosure defined by the housing and a movable, liquid impermeable partition between the enclosure and the aforementioned chamber. The partition is preferably a flexible member such as a diaphragm or bellows, but can also be a piston, or like means that provides for substantial equalization of pressure between the enclosure and the chamber. The primary flow path includes a first fluid passageway which is in fluid communication with the inlet for the primary medication, the variable volume enclosure and a second fluid passageway that provides communication between the variable volume enclosure and the mixing cell.

A positive fluid pressure at the inlet also generates a positive fluid pressure through the first fluid passageway into the enclosure. This positive fluid pressure is then transmitted across the movable partition to pressurize the chamber as well. The positive fluid pressure in the chamber drives the secondary medication to the mixing cell through the second medication fluid passageway. Since the volume of the chamber is itself reduced as a result, air is not introduced into the chamber. Thus, as the medication is dispensed therefrom, the likelihood of contamination is substantially eliminated. The primary medication continues to flow through a second fluid passageway forming part of the primary flow path to the mixing cell.

The mixing cell can be a drip chamber having an outlet to the patient and is preferably mounted on the housing such that the housing defines the upper portion of the device and the mixing cell defines the lower portion of the device. The outlet of the mixing cell is preferably at the bottom portion of the cell. Since the same pressure head provides the driving force for all medications delivered by the device of this invention, the same chosen dilution is maintained throughout delivery. Unlike previous systems, separate reservoirs at particular heights for each medication to be delivered are not required.

Appropriate flow regulating means can be associated with each of the medication flow paths to regulate the flow of respective medications into the mixing cell. The fluid regulating means can be adjustable tubing clamps that are set by thumbscrews. The total volumetric rate administered as well as the dilution of the second medication being introduced to the patient can be independently regulated and set as desired. This allows potentially infinite dilution ratios and a wide range of volumetric ratios of administration. After all of the secondary medication has been mixed and administered to the patient, the device will automatically continue to administer the primary medication. No further setting or adjustment is needed.

Because the present invention only requires a single passageway communicating with a single external reservoir, the secondary medication reservoir does not have to be positioned at a specific, different elevation and therefore at a different pressure head. Likewise, only a single tube runs from the device to the patient. This reduces both the cost and complexity of the administration and eliminates the maze of tubing common in prior art delivery devices.

Numerous other advantages and features of the present invention will become readily apparent from the following detailed description of the preferred embodiment of the invention, the drawings, and the appended claims.

DESCRIPTION OF THE PREFERRED EMBODIMENT

Figure 1:
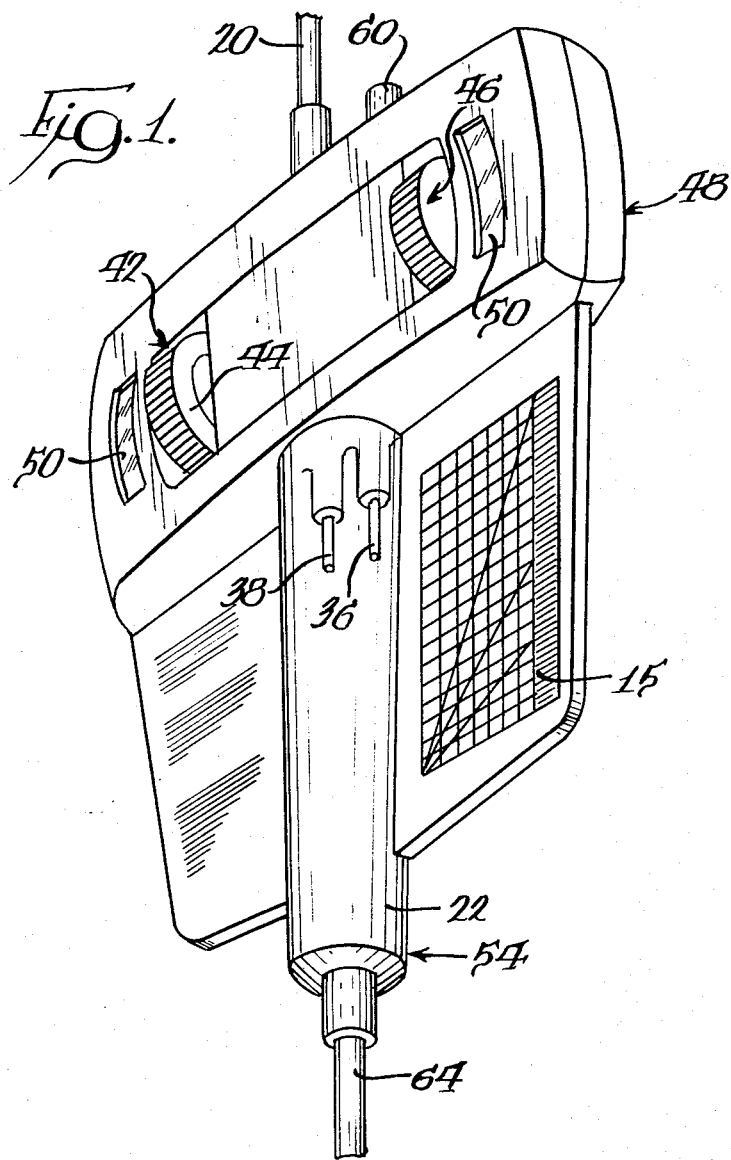
FIG. 1 is a perspective view of a medication mixing device embodying the present invention.

While this invention can be embodied in many forms, there is shown in the drawing and will be described in detail, a preferred embodiment of the invention. The present disclosure is an exemplification of the principles of the invention, and is not intended to limit the invention to the embodiment illustrated.

The present invention is a medication mixing device which allows for the mixing and diluting of secondary medication in a primary medication as the primary medication is being administered to a patient. The primary medication is usually a physiologically acceptable liquid such as saline, dextrose, or the like. The secondary medication can be medication in a liquid form which can be administered over time and perferably is diluted before administration.

Figure 2:
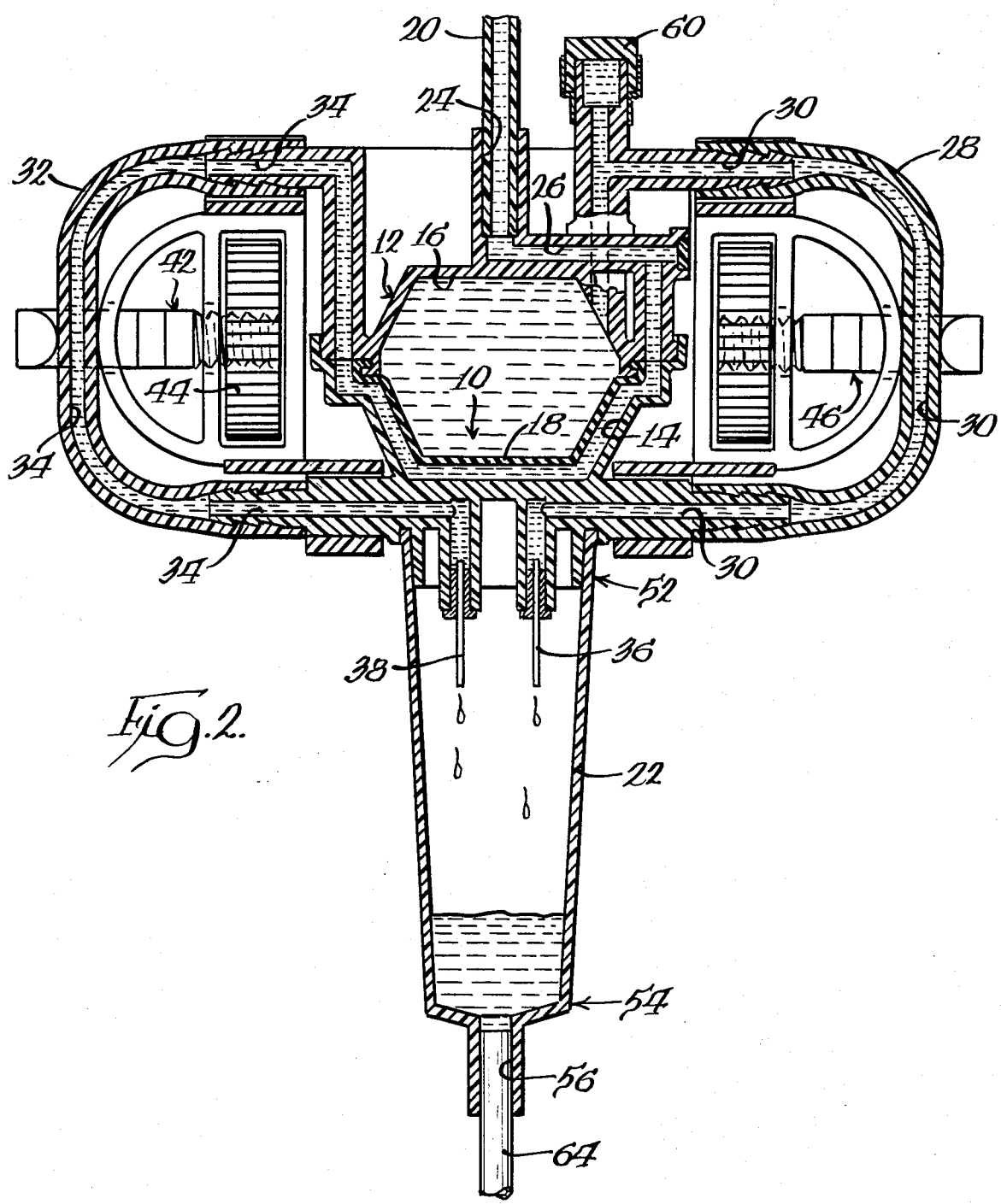
FIG. 2 is an elevational view partly in section, showing the internal components of the medication mixing device shown in FIG. 1.

A preferred embodiment of the medication mixing device is shown in FIGS. 1 and 2. The medication mixing device generally includes an exterior protective case 48 carrying flow regulating means 42 and 46, mixing cell or drip chamber 22, and connecting tubing 20 and 64. Flow adjustment chart 15 can also be provided on case 48. A housing 12 (FIG. 2) is contained within case 48 and defines a first, confined but variable volume space or chamber 16 and a second confined but variable volume space or enclosure 14 separated by a movable partition or a flexible member 18. The chamber 16 is adapted to receive and hold a medication to be administered to the patient. The enclosure 14 and flexible member 18 serve as part of a volume reducing means 10 which decreases the volume of the chamber 16 to deliver medication from the chamber to the mixing cell 22.

The device of this invention also includes an inlet 24 for receiving a primary medication from the primary medication supply (not shown) through a first tube 20. The primary medication flows through a primary flow path which includes a first fluid passageway 26, enclosure 14 and a second fluid passageway 34. The inlet 24 which is preferably mounted on the top of the housing 12 is in fluid communication with the enclosure 14 through the first fluid passageway 26. The first fluid passageway 26 is preferably defined by the housing 12.

A positive fluid pressure at the inlet 24 generates through the first fluid passageway 26 an equal fluid pressure in the enclosure 14. Through the flexible member 18 this fluid pressure generates a substantially equal fluid pressure in the chamber 16. Medication is then displaced out of the chamber and into the cell 22 through a secondary medication fluid passageway 30 which can be defined in part by a flexible secondary medication tube 28.

The inlet 24 is also in fluid communication with the cell 22 through the second fluid passageway 34 which can be defined in part by a flexible primary medication tube 32. The second fluid passageway 34 communicates with the enclosure and can communicate directly from the inlet 24 to the cell 22, or as shown in FIG. 2, communicate with the inlet through the enclosure 14 and first fluid passageway 26. It is preferred that the flow of liquid be through the first fluid passageway 26, entering one side of the enclosure 14, passing across the enclosure, and out through the other side of the enclosure into the second fluid passageway 34. Such a flow-through system avoids the entrapment of air within the enclosure 14 which can interfere with the operation of the volume reducing means 10. The first and second fluid passageways need not communicate with the enclosure 14 on opposite walls. However, the first and second fluid passageways preferably are not in direct fluid communication with each other, but communicate through the enclosure 14.

Both the secondary medication and second fluid passageways are preferably provided with drip cannulae 36 and 38 respectively which generate drops of fluid having a predetermined volume and thus provide a convenient metering means. Generally, it is preferred to use cannulae of a size which produce 60 drops per milliliter. This allows for visual determination of the rate of primary medication introduction into the cell 22 through cannula 38 and of the rate of secondary medication introduction into the cell through cannula 36. The ratio of these rates provides the dilution while the the sum of the two is the amount of total fluid being administered to the patient per unit time. The primary medication drip rate from cannula 38 is the rate at which the primary medication is introduced to the patient after the medication supply has been exhausted.

Preferably, a first or primary medication flow regulating means 42 is associated with the second fluid passageway for controlling the flow of primary medication into the cell 22. This regulator means is preferably a clamp mechanism having an adjustable screw 44 which can progressively squeeze the primary medication tube 32 to reduce the flow of primary medication through the second fluid passageway. A second or secondary medication flow regulating means 46 is also preferably associated with the second fluid passageway for controlling the flow of secondary medication into the cell 22. For simplicity of construction, the second flow regulating means can be of the same construction as the first. The position of the flow regulators at any given time can be seen through windows 50 on exterior protective case 48.

The medical device is preferably operated as a gravity system so that the housing 12 defines the upper portion of the device and the cell 22 defines the lower portion of the device. The cell 22 has a bottom portion 54 and the top portion 52 sealingly mounted on the housing 12. The bottom portion defines an outlet 56 through which the resulting mixture of medications can be delivered to the patient. The cannulae 36 and 38 are preferably located in the upper portion 52 of the cell spaced from the outlet 56 so that their respective medications can drip into the cell allowing for counting and mixing in the bottom portion 54 of the cell. The chamber 16 is positioned above the enclosure 14 to ensure that only fluid pressure drives medication to the cell 22. Locating the secondary medication fluid passageway connection above the chamber 16 also prevents syphoning and allows for air to be easily purged from the chamber.

In operation, a primary medication source such as a collapsible bag of saline (not shown) is connected as by the first tube 20 to the inlet 24. The saline bag should be elevated above the device or alternatively the saline pumped into the device under pressure. Secondary medication can be introduced into the chamber 16 through a resealing injection port 60 with a hypodermic syringe or singular device. The secondary medication can be first diluted in a suitable physiologically tolerable solution such as saline before being introduced into the chamber 16.

The primary medication enters the device through the inlet 24, and passes through the first passageway 26, into the enclosure 14. A portion of the primary medication exits the enclosure 14 into the second passageway, and through cannula 38 into the mixing cell 22. The remainder of the primary medication in the enclosure 14 generates a positive pressure against the flexible member 18 which drives the secondary medication from the chamber 16 to the cell 22. The first and second flow regulating means are adjusted to provide the desired dilution and rate of total flow. The primary medication then drips from the cannula 38 while the secondary medication drips from the cannula 36. As the medications drip into the cell 22 they mix in the bottom portion of the cell 54 and pass through outlet 56 and through a fourth tube 64 to the patient.

Since the head of pressure delivering the primary medication to the first flow regulating means 42 is substantially equal to the head of pressure delivering the secondary medication to the second flow regulating means 46, the respective drip rates and hence the dilution ratio remains substantially constant during the entire administration. After all of the secondary medication has been administered, the primary medication will continue to be administered. Thus not only a mixing of medications, but also an automatic sequential delivery of medications is achieved. If desired, more or different secondary medication can be added to the chamber 16 for further mixing and administration.

The flexible member 18 can be made of any suitable material, but is preferably a liquid impermeable diaphragm having a generally bellows configuration and is made of dipped or molded latex or vinyl. The flexible member 18 preferably is not under tension at any location between a full and empty chamber 16. Driving force in the chamber 16 is derived from the primary medication in the enclosure 14.

The chamber 16 and enclosure 14 preferably have circular cross-sections for best operation of the flexible member 18. The flexible member 18 has about the same general configuration as the chamber 16, e.g. frustoconical, so that it displaces substantially all of the secondary medication. The relative sizes of the enclosure 14 and chamber 16 change as the secondary medication is delivered. As shown in FIG. 2, the secondary medication has just begun to be delivered from the device.

Instead of a flexible member 18 such as a membrane, a sliding piston-like partition can be used as part of the volume reducing means. In such a case, the chamber, the enclosure and the partition have a coacting and sealing cylindrical configuration.

The medication mixing device of this invention not only serves as a reservoir for storing the secondary medication until it is delivered to the patient, but also ensures that the secondary medication is diluted at a substantially constant rate as it is being administered to the patient. Because only a single tube 20 is connected to a primary medication reservoir, the present invention is easy to set up while the flow regulating means provide for easy adjustment.

The housing 12 and cell 22 can be made of any suitable plastic material with the cell being made of a substantially transparent or clear plastic material. The tubes 28 and 32 are preferably made of a medical grade flexible plastic material such as those derived from organosilicon polymers which minimize plastic creep. Particularly suitable is Silastic (tradename of Dow Corning, of Midland, Mich.). This allows for inexpensive construction which is important in a hospital setting where it is preferred to use a disposable device.

What is claimed is:

1. A medication mixing device for use with a primary medication source, the device comprising:
   (a) a housing defining a first confined space and a second confined space separated by a movable partition, the first space being adapted to receive a secondary medication;

(b) a mixing cell mounted on the housing and having an outlet;

(c) an inlet on the housing for receiving primary medication from the primary medication source;

(d) a secondary medication fluid passageway in fluid communication with the first confined space and the cell;

(e) a first fluid passageway in fluid communication with the inlet and the second confined space;

(f) a second fluid passageway in fluid communication with the inlet, the first fluid passageway and the mixing cell such that a positive fluid pressure at the inlet generates a positive fluid pressure in the second confined space to drive the partition so as to displace secondary medication from the first confined space into the cell to mix with primary medication entering the cell through the second passageway.

2. The medication mixing device of claim 1 wherein the partition includes a flexible member.

3. The medication mixing device of claim 1 including primary medication flow regulating means associated with the second fluid passageway for regulating the flow of primary medication into the cell.

4. The medication mixing device of claim 1 including secondary medication flow regulating means associated with the secondary medication fluid passageway for regulating the flow of secondary medication into the cell.

5. The medication mixing device of claim 1 wherein the second and secondary medication fluid passageways are defined in part by flexible tubes.

6. The medication mixing device of claim 1 wherein the housing defines the upper portion of the device and the cell defines the lower portion of the device.

7. The medication mixing device of claim 6 wherein the variable cross-section fluid passageways open into the mixing cell spaced above the cell outlet.

8. The medication mixing device of claim 6 wherein the first confined space is located above the second confined space.

9. The medication mixing device of claim 1 including an injection port associated with the secondary medication fluid passageway for introducing secondary medication into the second confined space.

10. The medication mixing device of claim 1 wherein the second and secondary medication fluid passageways each terminate in a cannula through which each passageway communicates with the cell, the cannulae being adapted to produce drops having a predetermined volume.

11. The medication mixing device of claim 1 wherein the second fluid passageway communicates with the inlet through the first fluid passageway.

12. The medication mixing device of claim 11 wherein the first variable second fluid passageway communicates with the first fixed fluid passageway through the first confined space.

13. A medication diluting device for use with a diluent supply, the device comprising:
  (a) a housing defining an enclosure and a chamber separated by a flexible member, the chamber being adapted to receive a medication;
  (b) a mixing cell having a top portion and a bottom portion and an outlet on the bottom portion, the top portion of cell being mounted on the housing;
  (c) an inlet mounted on the housing for receiving diluent from the diluent supply;
  (d) a medication fluid passageway in fluid communication between the chamber and opening into the top portion of the cell;
  (e) a first fluid passageway in fluid communication with the inlet and the enclosure;
  (f) a second fluid passageway in fluid communication with the enclosure and opening into the top portion of the mixing cell such that a positive fluid pressure at the inlet generates a positive pressure in the enclosure to drive the flexible member to reduce the chamber volume and displace medication from the chamber and into the cell to mix with diluent entering the cell through the third passageway;
  (g) diluent flow regulating means associated with the second fluid passageway for regulating the flow of liquid into the cell; and
  (h) medication flow regulating means cooperating with the medication fluid passageway for regulating the flow of medication into the cell.

14. The medication diluting device of claim 13 wherein the medication and second fluid passageways each include a cannula through which each passageway communicates with the cell, the cannulae being adapted to produce drops of fluid having a predetermined volume.

15. The medication diluting device of claim 13 including an injection port associated with the chamber for introducing medication into the chamber.

16. The medication diluting device of claim 13 wherein the housing defines the upper portion of the device and the chamber is above the enclosure.

* * * * *